United States Patent
Shelton, IV et al.

(10) Patent No.: US 7,055,731 B2
(45) Date of Patent: Jun. 6, 2006

(54) SURGICAL STAPLING INSTRUMENT INCORPORATING A TAPERED FIRING BAR FOR INCREASED FLEXIBILITY AROUND THE ARTICULATION JOINT

(75) Inventors: Frederick E. Shelton, IV, Hillsboro, OH (US); Michael Earl Setser, Burlington, KY (US); William Bruce Weisenburgh, II, Maineville, OH (US)

(73) Assignee: Ethicon Endo-Surgery Inc., Cincinnati, OH (US)

( * ) Notice: Subject to any disclaimer, the term of this patent is extended or adjusted under 35 U.S.C. 154(b) by 50 days.

(21) Appl. No.: 10/615,974

(22) Filed: Jul. 9, 2003

(65) Prior Publication Data

US 2005/0006431 A1  Jan. 13, 2005

(51) Int. Cl.
*A61B 17/068* (2006.01)
(52) U.S. Cl. .................. 227/176.1; 227/19; 227/180.1
(58) Field of Search ............................ 227/19, 176.1, 227/180.1, 175.1; 606/146; 600/205
See application file for complete search history.

(56) References Cited

U.S. PATENT DOCUMENTS

| | | | |
|---|---|---|---|
| 5,031,814 A | 7/1991 | Tompkins et al. | |
| 5,071,052 A | 12/1991 | Rodak et al. | |
| 5,137,198 A | 8/1992 | Nobis et al. | |
| 5,312,023 A * | 5/1994 | Green et al. | 227/175.1 |
| 5,397,046 A | 3/1995 | Savage et al. | |
| 5,413,267 A | 5/1995 | Solyntjes et al. | |
| 5,413,268 A | 5/1995 | Green et al. | |
| 5,445,304 A | 8/1995 | Plyley et al. | |
| 5,484,095 A | 1/1996 | Green et al. | |
| 5,535,937 A | 7/1996 | Boiarski et al. | |
| 5,584,425 A | 12/1996 | Savage et al. | |
| 5,680,983 A | 10/1997 | Plyley et al. | |
| 5,704,534 A * | 1/1998 | Huitema et al. | 227/175.1 |
| 5,709,334 A | 1/1998 | Sorrentino et al. | |
| 5,735,445 A | 4/1998 | Vidal et al. | |
| 5,743,456 A * | 4/1998 | Jones et al. | 227/176.1 |
| 5,797,537 A * | 8/1998 | Oberlin et al. | 227/176.1 |
| 5,797,538 A * | 8/1998 | Heaton et al. | 227/176.1 |
| 5,901,895 A * | 5/1999 | Heaton et al. | 227/176.1 |
| 5,918,791 A | 7/1999 | Sorrentino et al. | |
| 6,032,849 A | 3/2000 | Mastri et al. | |
| 6,079,606 A | 6/2000 | Milliman et al. | |
| 6,109,500 A | 8/2000 | Alli et al. | |
| 6,202,914 B1 * | 3/2001 | Geiste et al. | 227/176.1 |
| 6,644,532 B1 * | 11/2003 | Green et al. | 227/176.1 |
| 6,681,978 B1 * | 1/2004 | Geiste et al. | 227/176.1 |
| 2001/0029384 A1 | 10/2001 | Nicholas et al. | |
| 2004/0050902 A1 | 3/2004 | Green et al. | |

FOREIGN PATENT DOCUMENTS

DE   195 20 717 A1   12/1996

* cited by examiner

*Primary Examiner*—Stephen F. Gerrity
*Assistant Examiner*—Paul Durand (57) ABSTRACT

A surgical stapling and severing instrument particularly suited to endoscopic articulates an end effector by having a geared articulation mechanism that converts rotational motion from a handle portion. A firing bar longitudinally translates between the handle portion and the end effector. The firing bar head is thickened in order to present an undistorted cutting edge and engagement features to the opposing jaws of the end effector. The firing bar also advantageously includes a thinned or tapered proximal portion in the form of a strip or band that negotiates the articulation mechanism.

10 Claims, 10 Drawing Sheets

SURGICAL STAPLING INSTRUMENT INCORPORATING A TAPERED FIRING BAR FOR INCREASED FLEXIBILITY AROUND THE ARTICULATION JOINT

CROSS REFERENCE TO RELATED APPLICATIONS

The present application is related to four co-pending and commonly-owned applications filed on even date herewith, the disclosure of each is hereby incorporated by reference in their entirety, these four applications being respectively entitled:

(1) "SURGICAL INSTRUMENT INCORPORATING AN ARTICULATION MECHANISM HAVING ROTATION ABOUT THE LONGITUDINAL AXIS" to Kenneth S. Wales, Douglas B. Hoffman, Frederick E. Shelton IV, and Jeff Swayze;

(2) "SURGICAL STAPLING INSTRUMENT INCORPORATING AN ARTICULATION JOINT FOR A FIRING BAR TRACK" to Douglas B. Hoffman;

(3) "SURGICAL STAPLING INSTRUMENT HAVING ARTICULATION JOINT SUPPORT PLATES FOR SUPPORTING A FIRING BAR" to Kenneth S. Wales and Joseph Charles Hueil; and (4) "A SURGICAL INSTRUMENT WITH A LATERAL-MOVING ARTICULATION CONTROL" to Kenneth S. Wales.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that include an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician, this long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. Appl. Ser. No. 10/443,617, "SURGICAL STAPLING INSTRUMENT INCORPORATING AN E-BEAM FIRING MECHANISM" to Shelton et al., filed on 20 May 2003, describes an improved "E-beam" firing bar for severing tissue and actuating staples. Some of the additional advantages include affirmatively space the jaws of the end effector, even if slightly too much or two little tissue is clamped for optimal staple formation. Moreover, the E-beam firing bar includes engages the end effector and staple cartridge in a way that enables several beneficial lockouts to be incorporated.

Depending upon the nature of the operation, it may be desirable to further adjust the positioning of the end effector of an endoscopic surgical instrument rather than being limited to insertion and rotation. In particular, it is often desirable to orient the end effector at an axis transverse to the longitudinal axis of the shaft of the instrument. The transverse movement of the end effector relative to the instrument shaft is conventionally referred to as "articulation". This articulated positioning permits the clinician to more easily engage tissue in some instances. In addition, articulated positioning advantageously allows an endoscope to be positioned behind the end effector without being blocked by the instrument shaft.

While the aforementioned non-articulating stapling and severing instruments have great utility and may be successfully employed in many surgical procedures, it is desirable to enhance their operation with the ability to articulate the end effector, thereby giving greater clinical flexibility in their use.

Approaches to articulating a stapling and severing tend to be complicated by integrating control of the articulation along with the control of closing the end effector to clamp tissue and firing (i.e., stapling and severing) the end effector within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

While these longitudinally controlled articulation mechanisms have provided certain advantages to surgical instruments such as for endoscopic stapling and severing, it is believed that an alternative articulation motion would provide additional design flexibility. In particular, advantageous approaches are described in the four above cross-referenced and co-pending applications wherein a rotational motion relative to a longitudinal axis of the shaft transfers an articulating motion to an articulation mechanism coupling the end effector to the shaft.

What would be further desirable is to retain the advantages of an E-beam firing bar in a surgical stapling and severing instrument in combination with a rotationally controlled articulation mechanism. Consequently, a significant need exists for such an instrument incorporating a firing beam that advantages severs clamped tissue, engages the jaws of the end effector for affirmatively-controlled stapling, yet is coupled for firing motion through an articulation mechanism.

SUMMARY OF THE INVENTION

The invention overcomes the above-noted and other deficiencies of the prior art by providing a firing bar that is effective in longitudinally actuating an end effector and also has a tapered proximal portion that is effective in flexing through an articulating shaft. Thereby, the clinical advantages of an articulating surgical instrument are realized without degrading consistent operation of the end effector.

On one aspect of the invention, a surgical instrument has a handle portion that produces an articulation motion and a firing motion that are transferred through a shaft having a longitudinal axis. An articulation mechanism coupling the shaft to an end effector and responsive to the articulation motion to rotate the end effector from the longitudinal axis of the shaft. A firing mechanism responds to the firing motion and is coupled for movement through the articulation mechanism and end effector. In particular, the firing mechanism has an actuating portion having a first thickness and positioned in the end effector and an articulation portion proximally attached to the actuating portion and having a second thickness less than the first thickness for articulating movement through the articulation mechanism. Thereby the firing mechanism is effective at both actuating the end effector and articulating through the articulation mechanism.

In another aspect of the invention, a surgical instrument has a handle portion that produces a firing motion, a closing motion, and an articulation motion, with all threw separately transferred down a shaft. An end effector is pivoted by an articulation mechanism responsive to the articulation motion. The end effector includes an elongate channel coupled to the shaft and including a channel slot. An anvil is pivotally coupled to the elongate channel and is responsive to the closing motion from the shaft and has an anvil channel. A firing device has a distally presented cutting edge longitudinally received between the elongate channel and the anvil and includes a thinned strip portion transitioning through the articulation mechanism.

In yet another aspect of the invention, a surgical instrument has a handle portion operably configured to produce a rotational articulation motion and a longitudinal firing motion, which are transferred through a shaft. An articulation mechanism responds to the rotational articulation motion to articulate an end effector. A firing bar responds to the longitudinal firing motion of the handle portion. The firing bar includes an elongate strip longitudinally positioned for movement through the articulation mechanism and has a firing bar head distally connected to the elongate strip and positioned for longitudinal movement in the end effector.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
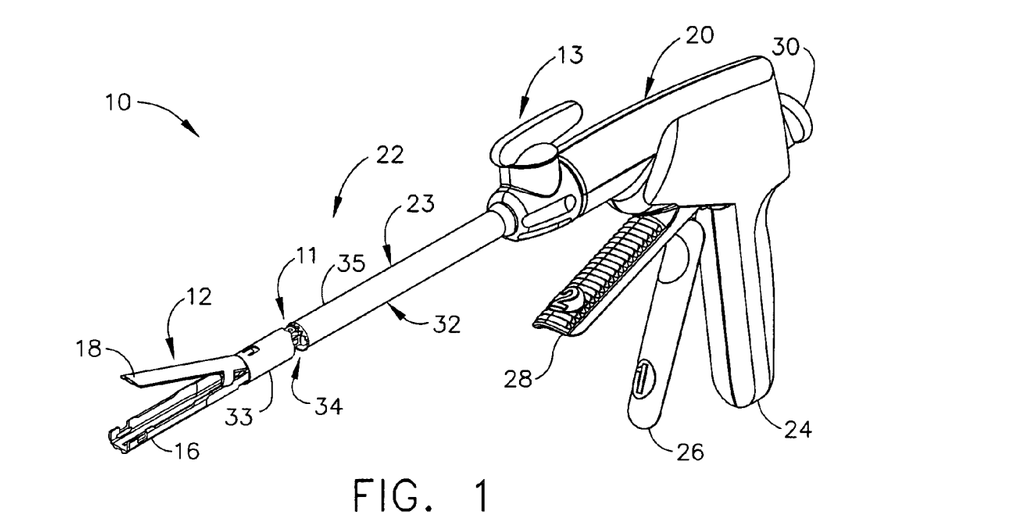
FIG. 1 is a perspective view of an articulating surgical instrument in a nonarticulated position.
Figure 2:
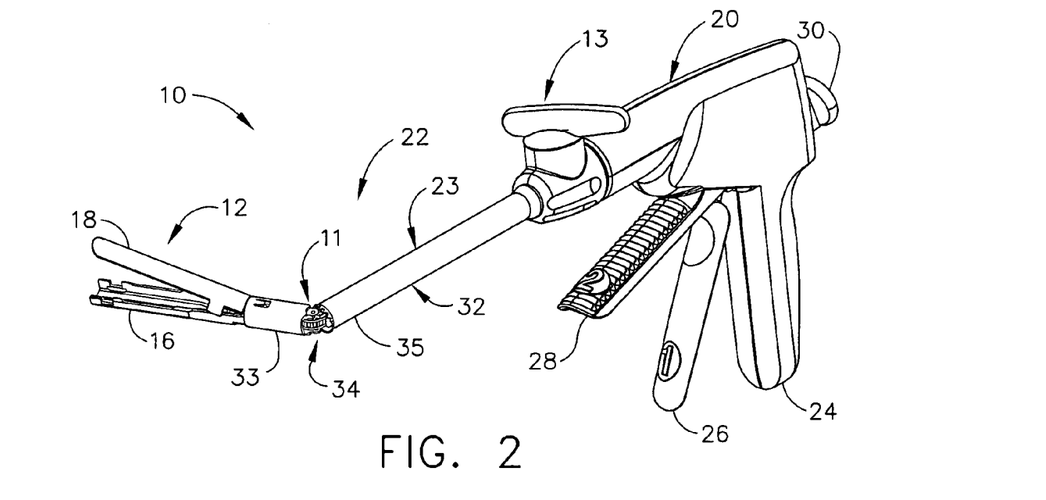
FIG. 2 is a perspective view of an articulating surgical instrument in an articulated position.
Figure 3:
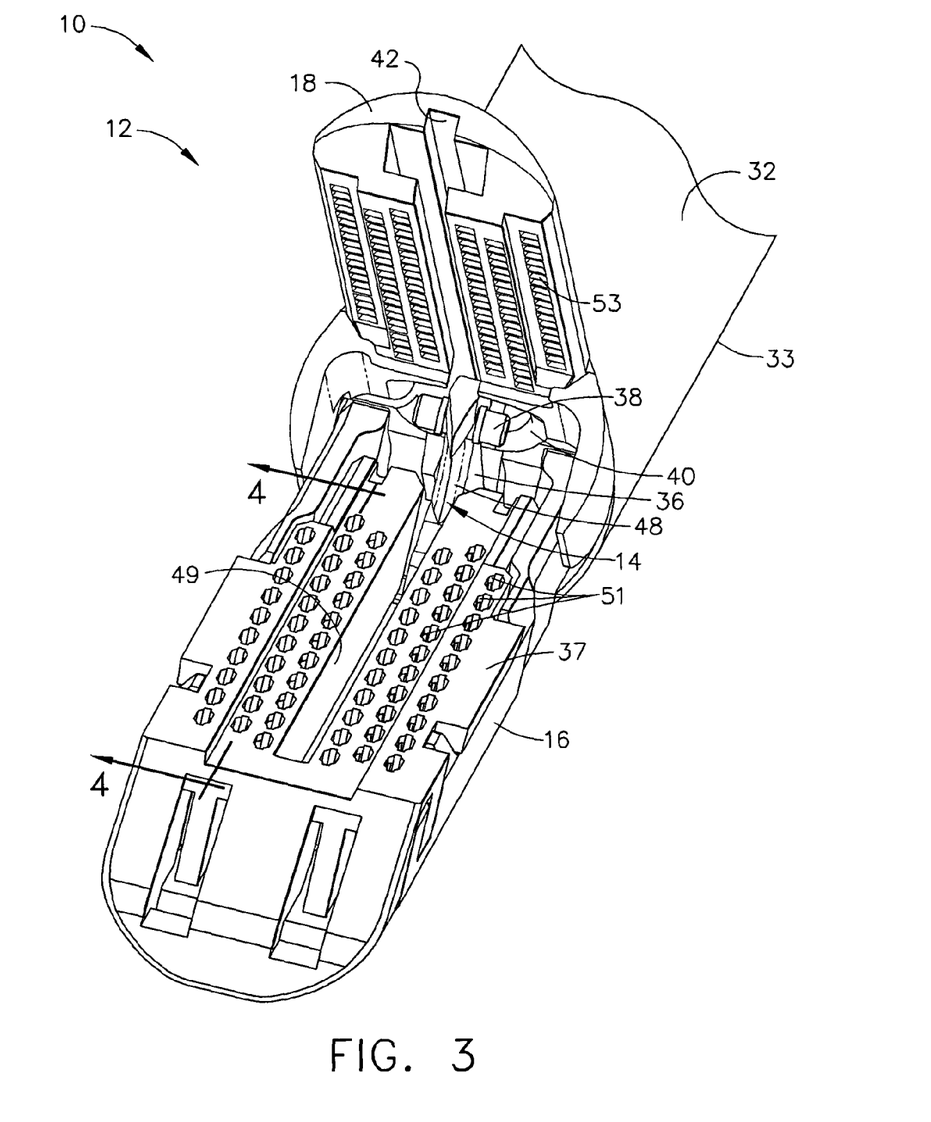
FIG. 3 is a perspective view of an opened end effector of the articulating surgical instrument of FIGS. 1–2.

Turning to the Drawings, wherein like numerals denote like components throughout the several views, FIGS. 1–3 depict a surgical instrument, which in the illustrative embodiment is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient for performing a surgical procedure. Once an articulation mechanism 11 and a distally attached end effector 12 are inserted through the cannula passageway, the articulation mechanism 11 may be remotely articulated, as depicted in FIG. 2, by an articulation control 13. Thereby, the end effector 12 may reach behind an organ or approach tissue from a desired angle or for other reasons. For instance, a firing mechanism, advantageously depicted as an E-beam firing bar 14 (depicted in FIG. 3), that severs clamped tissue, engages an elongate channel 16 and a pivotally attached anvil 18.

The surgical and stapling and severing instrument 10 includes a handle portion 20 connected to an implement portion 22, the latter further comprising a shaft 23 distally terminating in the articulating mechanism 11 and the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12. Thereafter, a release button 30 is depressed to release the clamped tissue.

An outmost closure sleeve 32 of the shaft 23 longitudinally translates in response to the closure trigger 26 to pivotally close the anvil 18. Specifically, a distal portion, or closure ring 33, of the closure sleeve 32 with respect to the articulation mechanism 11 is indirectly supported by a frame 34 of the implement portion 22 (partially visible at the articulation mechanism 11). At the articulation mechanism 11, a proximal portion, or closure tube 35, of the closure sleeve 32 communicates with the distal portion (closure ring) 33. The frame 34 is flexibly attached to the elongate channel 16 via the articulation mechanism 11, enabling articulation in a single plane. The frame 34 also longitudinally slidingly supports a firing drive member 36 that communicates a firing motion from the firing trigger 28 to the firing bar 14. Only the firing bar 14 of the firing drive member 36 is depicted FIG. 3, but the firing drive member 36 is described below further detail with regard to various versions of a rotationally controlled articulation mechanism 11.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

E-Beam Firing Bar

Figure 4:
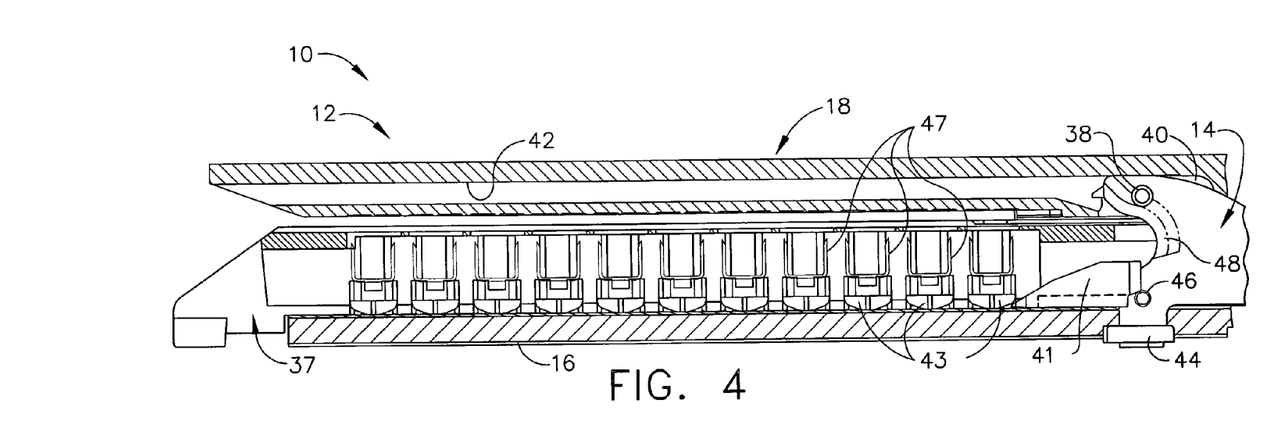
FIG. 4 depicts a side elevation view in section of the end effector of FIG. 3 of the surgical instrument of FIG. 1, the section generally taken along lines 4—4 of FIG. 3 to expose portions of a staple cartridge but also depicting the firing bar along the longitudinal centerline.
Figure 5:
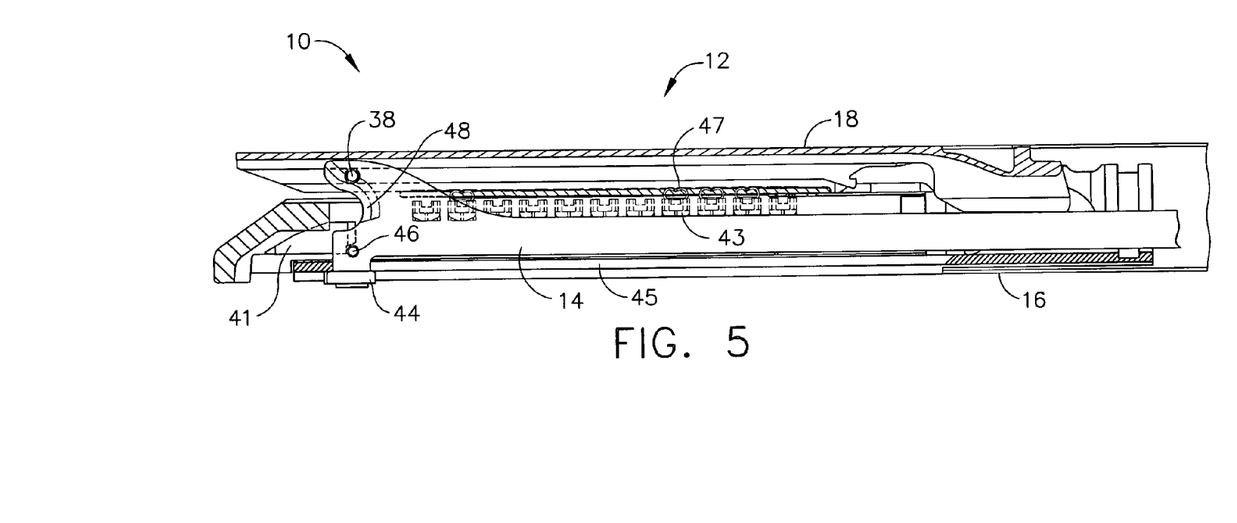
FIG. 5 depicts a side elevation view in section of the end effector of FIG. 4 after the firing bar has fully fired.

FIGS. 3–5 depict the end effector 12 employing the E-beam firing bar 14 to perform a number of functions. In FIG. 3, the firing bar 14 is proximally positioned, allowing an unspent staple cartridge 37 to be installed into the elongate channel 16. In particular, an upper pin 38 of the firing bar 14 resides within a recess, depicted as an anvil pocket 40 allowing the anvil 18 to be repeatedly opened and closed. With the end effector closed as depicted in FIG. 4, the firing bar 14 is advanced in engagement with the anvil 18 by having the upper pin 38 enter a longitudinal anvil slot 42. A lower most pin, or firing bar cap 44, engaged a lower surface of the elongate channel 16 by having the firing bar 14 extend through a channel slot 45. A middle pin 46 slidingly engages a top surface of the elongate channel 16, cooperating with the firing bar cap 44. Thereby, the firing bar 14 affirmatively spaces the end effector 12 during firing, overcoming pinching that may occur with a minimal amount of clamped tissue and overcoming staple malformation with an excessive amount of clamped tissue.

During firing, a distally presented cutting edge 48 between the upper pin 38 and middle pin 46 of the firing bar enters a proximally presented vertical slot 49 of the staple cartridge 37, severing tissue clamped between the staple cartridge 37 and the anvil 18. As shown in FIG. 4, the middle pin 46 actuates the staple cartridge 37 by entering into a firing slot within the staple cartridge 37, driving a wedge sled 41 into upward camming contact with staple drivers 43 that in turn drive a plurality of staples 47 out of staple apertures 51 in the staple cartridge 37 into forming contact with staple pockets 53 on an inner surface of the anvil 18.

FIG. 5 depicts the firing bar 14 fully distally translated after completing severing and stapling tissue.

Two-Axis Handle

Figure 6:
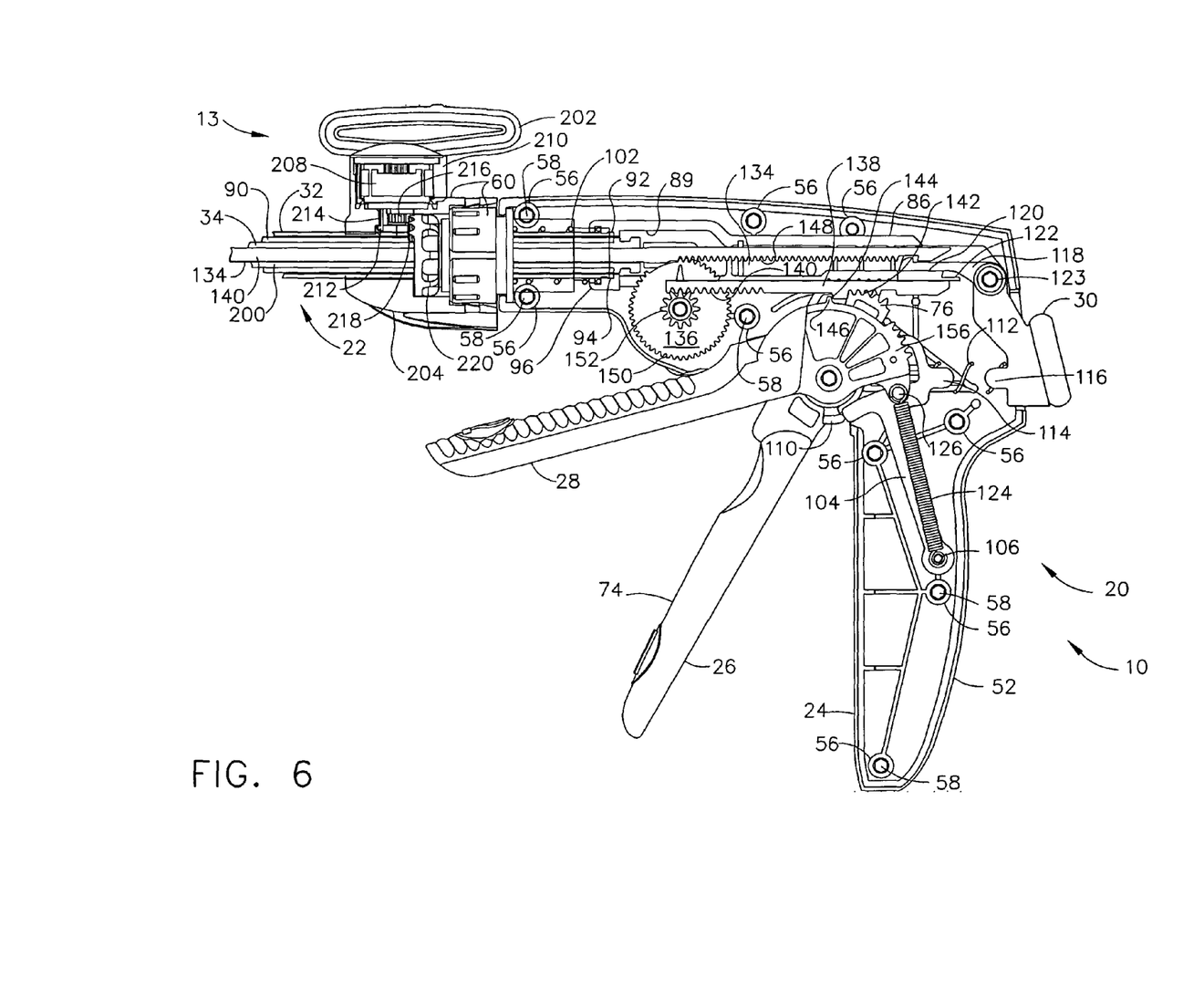
FIG. 6 depicts a side elevation view in section of a handle portion of a proximal end of the surgical instrument of FIG. 1 including a rotating articulation control.
Figure 7:
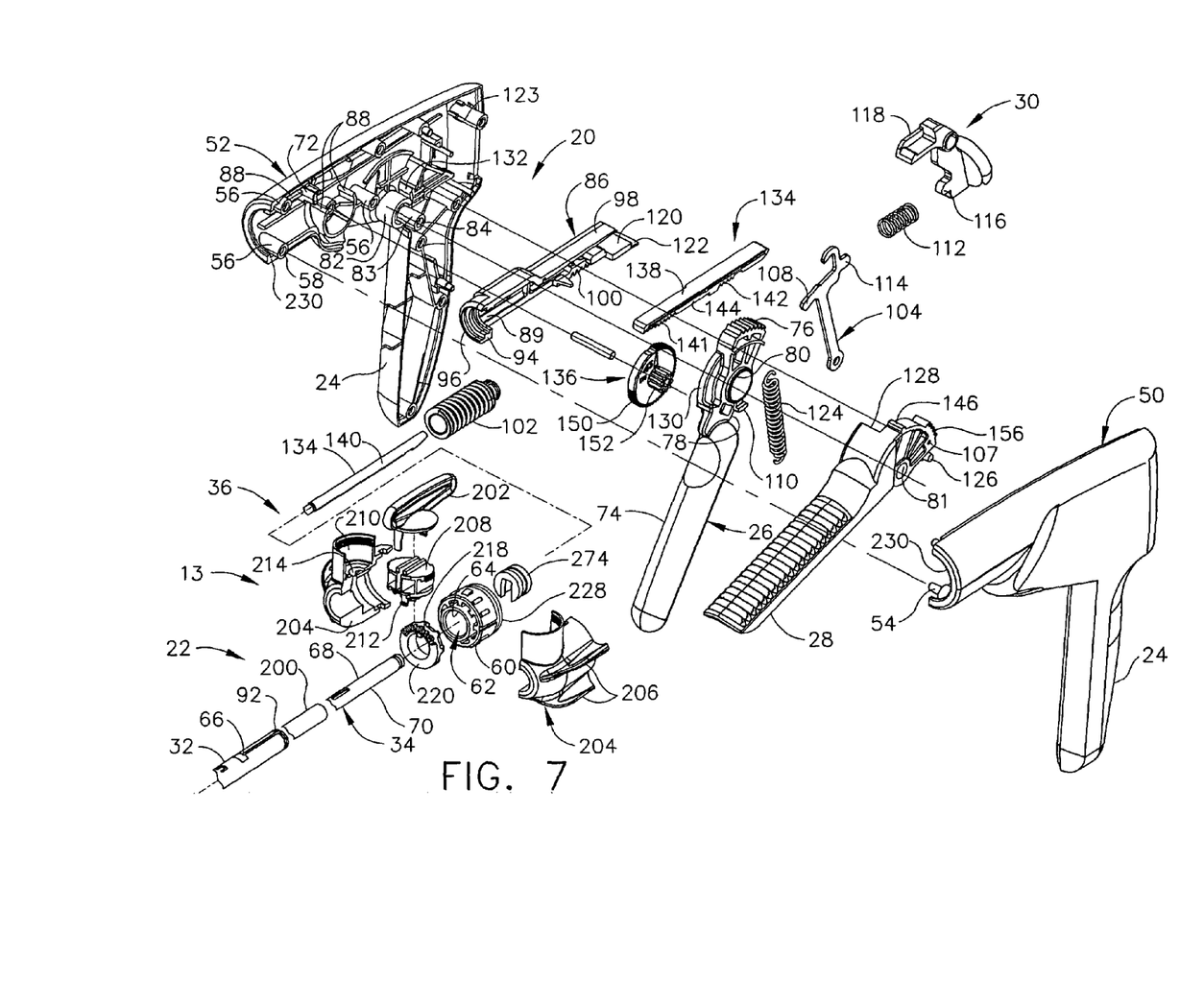
FIG. 7 depicts a perspective, exploded view of the handle portion of the proximal end of the surgical instrument of FIG. 1.
Figure 8:
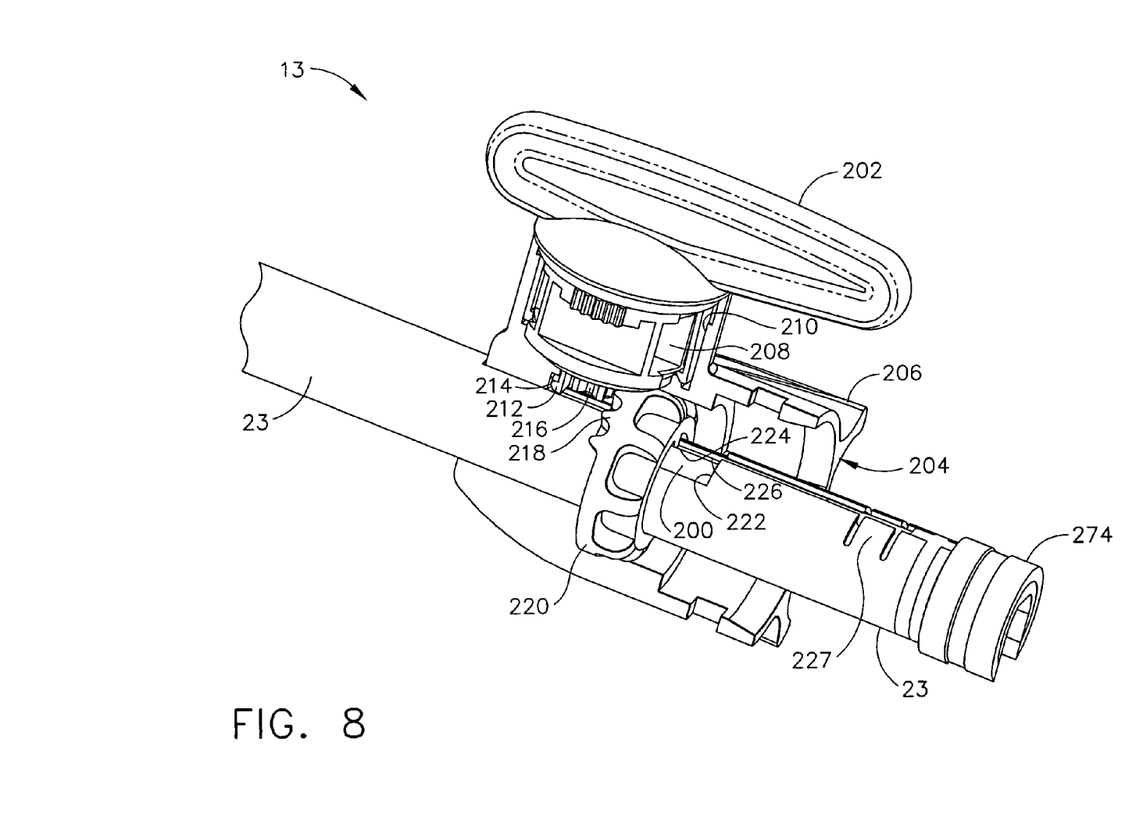
FIG. 8 depicts a perspective view looking downward, forward and to the right of a distal portion of the handle portion of the surgical instrument of FIG. 1 partially cutaway to expose a rotating articulation control mechanism.
Figure 9:
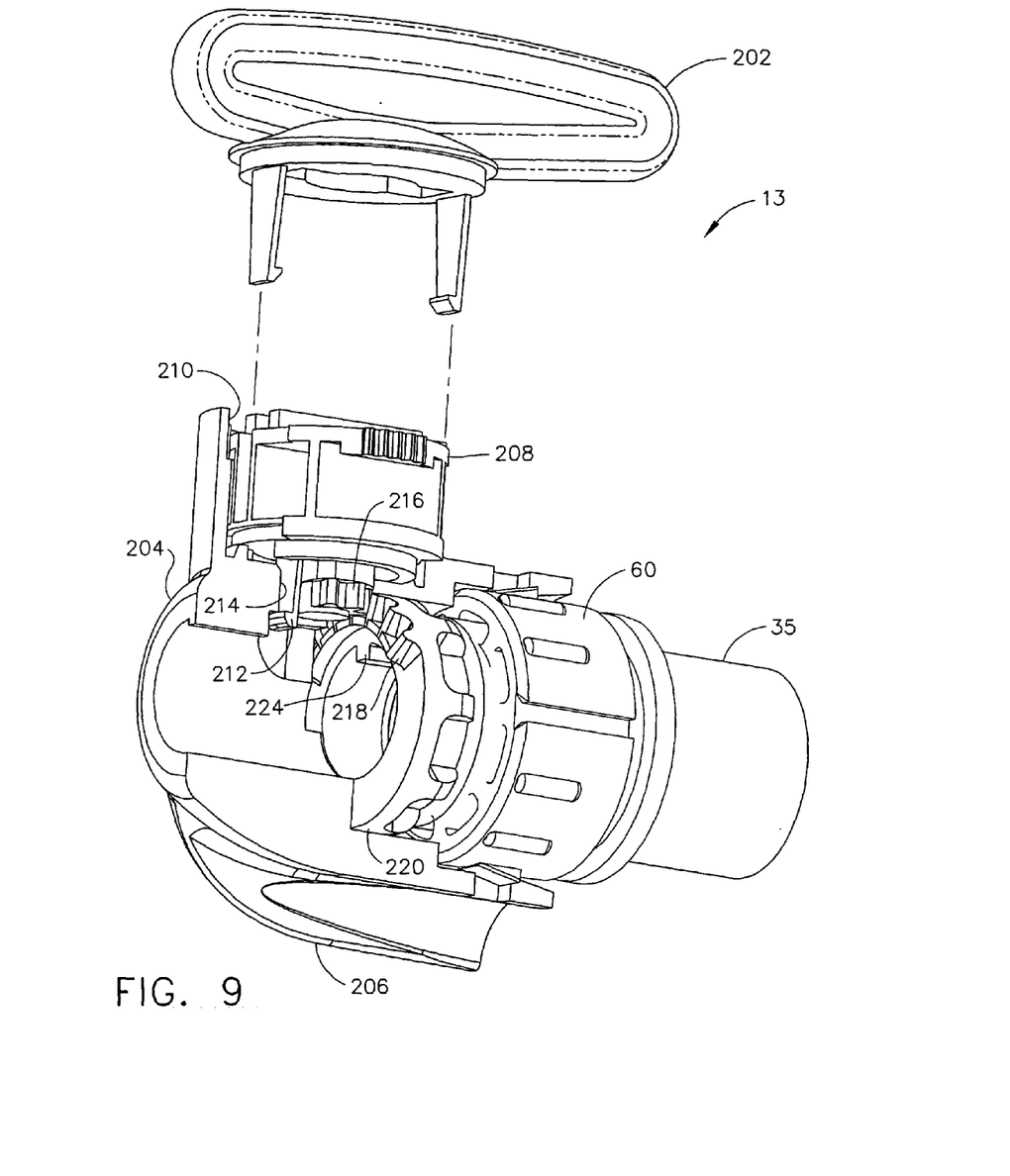
FIG. 9 depicts a perspective view looking upward, rearward and to the right of the distal portion of the handle portion of FIG. 8, partially cutaway to expose the rotating articulation control mechanism and have a rotating articulation control knob disassembled.

With reference to FIGS. 6–7, the handle portion 20 is comprised of first and second base sections 50 and 52, which are molded from a polymeric material such as a glass-filled polycarbonate. The first base section 50 is provided with a plurality of cylindrical-shaped pins 54. The second base section 52 includes a plurality of extending members 56, each having a hexagonal-shaped opening 58. The cylindrical-shaped pins 54 are received within the hexagonal-shaped openings 58 and are frictionally held therein for maintaining the first and second base sections 50 and 52 in assembly.

A housing cap 60 has a bore 62 extending completely through it for engaging and rotating the implement portion 22 about its longitudinal axis. The housing cap 60 includes an inwardly protruding boss 64 extending along at least a portion of the bore 62. The protruding boss 64 is received within a longitudinal slot 66 formed at a proximal portion of the closure sleeve 32 such that rotation of the housing cap 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 3–4) rotates with the housing cap 60.

A proximal end 68 of the frame 34 passes proximally through the housing cap 60 and is provided with a circumferential notch 70 that is engaged by opposing channel securement members 72 extending respectively from the base sections 50 and 52. Only the channel securement member 72 of the second base section 52 is shown. The channel securement members 72 extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotally mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 110 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled, or wedge sled, in the implement portion 22 (not shown in FIG. 6-7) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter that is smaller than the first diameter.

Rotational Articulation Control

With reference to FIGS. 6–9, the handle portion 20 advantageously incorporates the articulation control 13 that both rotates the implement portion 22 about the longitudinal axis of the surgical instrument 10 and articulates the end effector 12 to an angle with the longitudinal axis. A hollow articulation drive tube 200 is concentrically located within the closure sleeve 32 and is operably coupled to an actuation lever 202 such that rotation of actuation lever 202 rotates tube 200 about the longitudinal axis and causes perpendicular rotation or articulation of the closure ring 250 and end effector 12. This articulation of the closure ring 250 corresponds to the degree and direction of rotation of actuator lever 202 viewed and manipulated by the clinician. In the illustrative version, the relationship is one to one, with the degree of rotation of the actuator lever 202 corresponding to the degree of articulation from the longitudinal axis of the shaft 23, thus providing an intuitive indication to the clinician. It will be appreciated that other angular relationships may be selected.

The articulation control 13 includes a pair of mirrored articulation transmission housings 204 that are attached to the housing cap 60. Moreover, the articulation transmission housing 204 includes longitudinally aligned external tabs 206 that a clinician twists to effect rotation of the articulation transmission housing 204, and thus of the end effector 12, about the longitudinal axis of the implement portion 22. The actuator lever 202 is attached to a cylindrical articulation body 208 that resides within a cylindrical recess 210 opening generally upward and perpendicular to the shaft 23. The lowermost portion of the articulation body 208 includes prongs 212 that snap fit into an opening 214 in the articulation transmission housing 208 near to the shaft 23, the prongs 212 preventing the articulation body 208 from being withdrawn from the cylindrical recess 210.

Annularly presented gear teeth 216 are located about the lower portion of the articulation body 208 and mesh with teeth 218 on an articulation yoke 220. The articulation yoke 220 straddles an articulation rectangular window 222 formed in the closure sleeve 32. Closure sleeve 32 is slidably moveable within the articulation control 13 (in the longitudinal direction) to close and open the end effector 12. The articulation drive tube 200 moves longitudinally with the closure sleeve 32 relative to the fixed articulation control 13. Window 222 provides clearance for a boss 224 inwardly presented from the articulation yoke 220 that passes through the rectangular window 222 to engage a slot 226 in the articulation drive tube 200, longitudinally positioning the articulation drive tube 200 for rotational motion. The hollow articulation drive tube 200 extends longitudinally within the closure sleeve 32 from the articulation mechanism 11 and terminates distally before the locking tabs 227 of the closure sleeve 32. The tabs 227 are inwardly bent behind the proximal face of the articulation drive tube 200 and thereby retaining the articulation drive tube 200 in the shaft 23.

It should be appreciated that the articulation transmission housing 204 is operatively associated to the closure tube 35 of the shaft 23. The housing cap 60 retains the articulation yoke 220 in the articulation transmission housing 204 and retains the articulation control 13 within the handle portion 20 by presenting proximally an outer diameter circular groove 228 that engages a circular inward lip 230 at the distal opening of the assembled base sections 50, 52.

Figure 10:
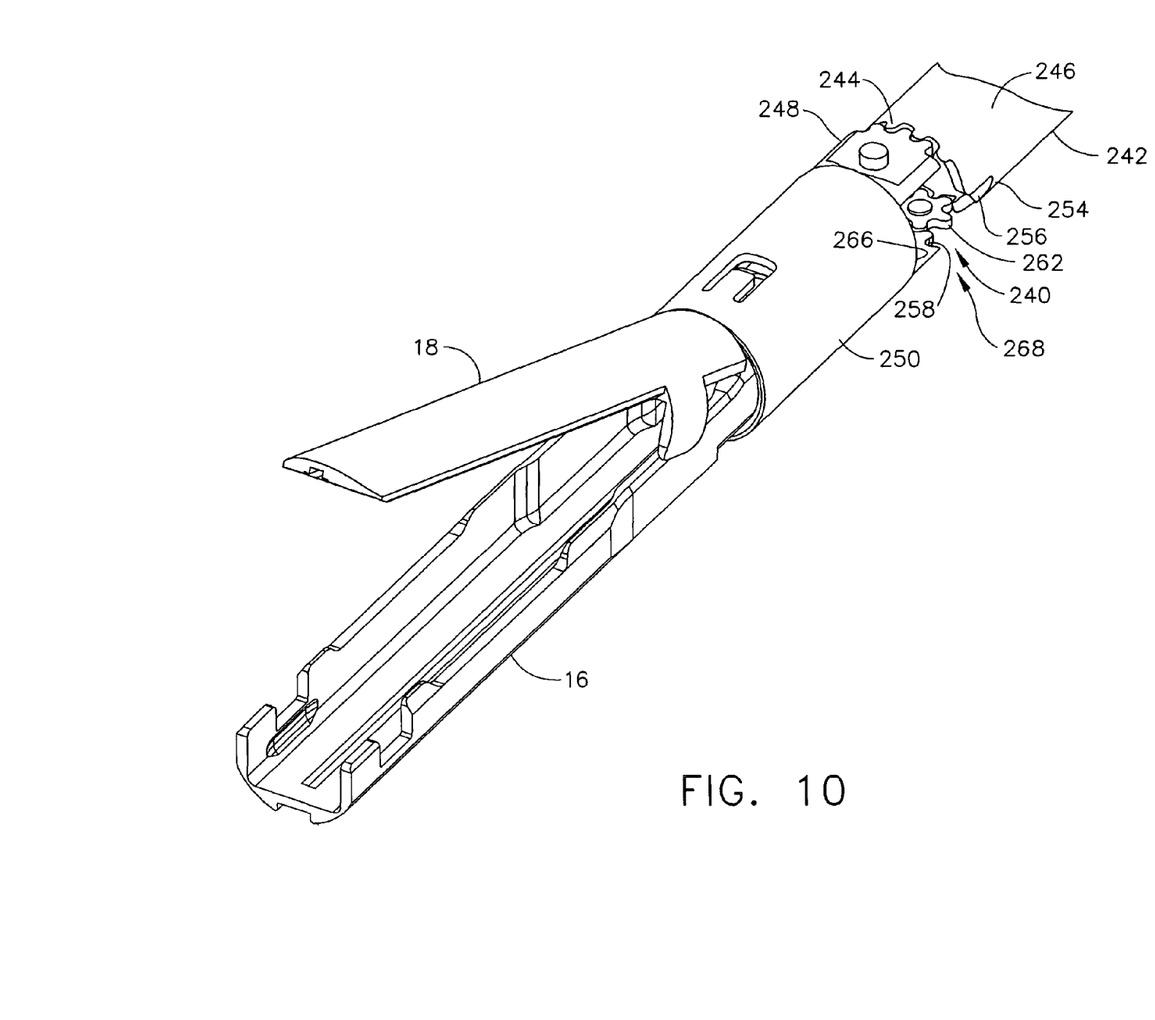
FIG. 10 depicts a top perspective detail view of a spur gear articulation mechanism and end effector of the surgical instrument of FIG. 1 with firing and frame portions removed.
Figure 11:
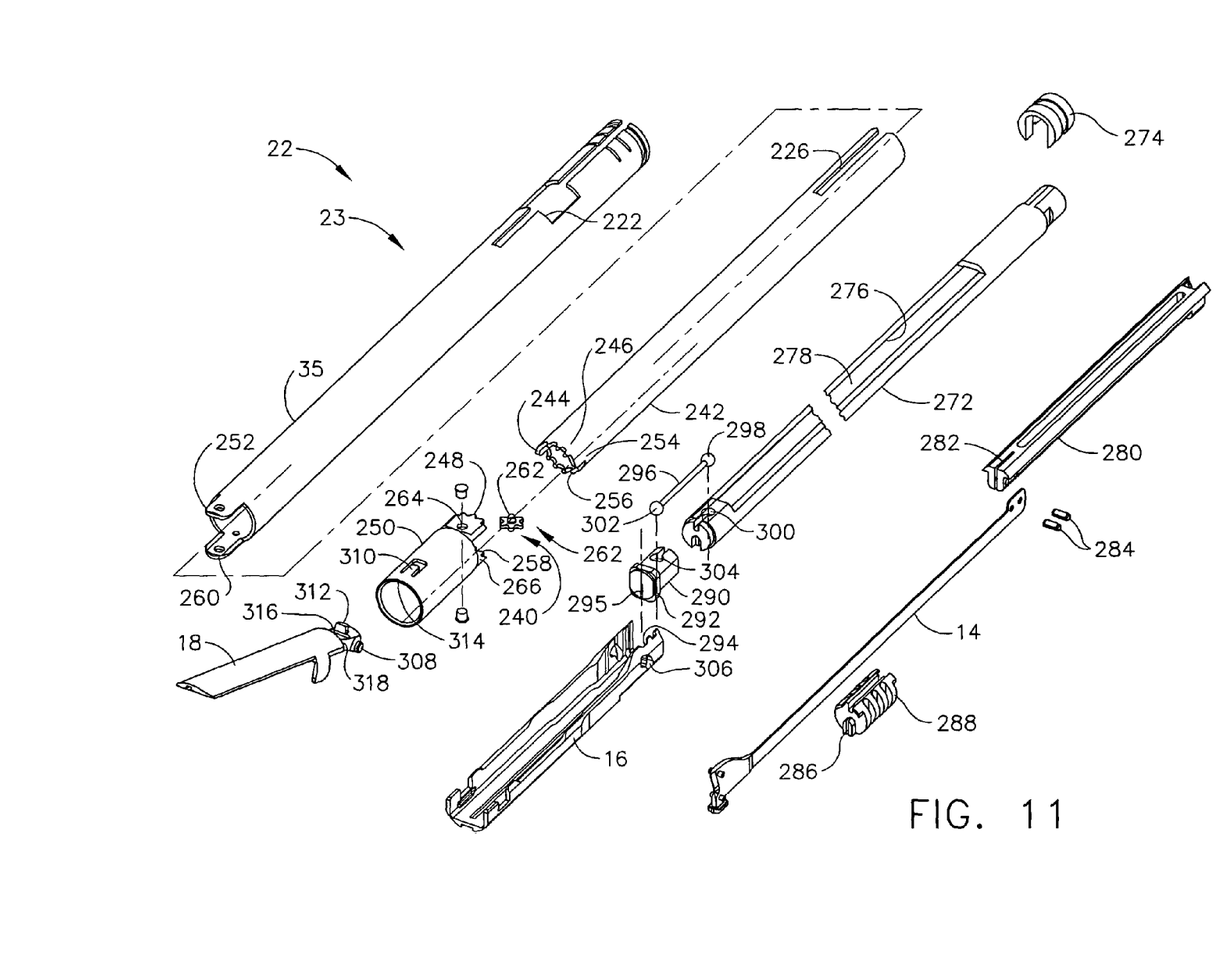
FIG. 11 depicts a perspective, exploded view of an implement portion of the surgical instrument of FIG. 1 including a spur gear articulation mechanism.

FIGS. 10 and 11 depict the gear articulation mechanism 11 of FIGS. 1–2 in the form of a spur gear articulation mechanism 240, which is generally the same as described above but with additional articulation driving components on the other side of the articulation mechanism 240 to thereby increase performance. Articulation mechanism 240 has a rotatable hollow articulation drive tube 242 that is concentrically located within closure sleeve 32 and has a distally projecting gear section 244 about a first circumference portion 246. Gear section 244 meshes with a spur gear 248 attached to and proximally projecting from closure ring 250 which pivots about pins 253 extending through first and second pivot points 252, 260 projecting distally from the closure sleeve 32. Thus, an articulation pivot axis passes through both the first and second pivot points 252, 260 and pins 253 rotatably couple closure ring 250 to the closure sleeve 32. Rotation of drive 242 engages the gears 242 and 248 and articulates closure ring 250 about first and second pivot points 252, 260.

To increase the effective surface area of gear contact between the hollow articulation drive tube 242 and the closure ring 250, a second circumference portion 254 of the hollow articulation drive tube 242 has a recessed distally projecting gear section 256 extending therefrom. Gear section 256 is operably coupled to a second spur gear 258 attached to and proximally projecting from an opposite lateral side of the closure ring 250 by a reversing gear 262 pivotally supported by the frame 34. Reversing gear 262 engages both the recessed distally projecting gear section 256 on one side and the second spur gear 258 of the closure ring 250 on the other.

When the closure trigger 26 is actuated, both the hollow articulation drive tube 242 and pivotally attached closure tube 250 of the closure sleeve 32 are moved distally to close the anvil 18. The closure tube 35 of the closure sleeve 32 is spaced away from the closure ring 33 by pivot points 252, 260 pinned to pivot holes 264 and 266 centered in spur gears 248, 258, and a frame opening 268 that extends therethrough. The frame opening 268 provides clearance so that the proximal edges of the closure ring 33 and the distal edges of the closure tube 35 of the closure sleeve 32 do not collide during articulation.

FIG. 11 depicts in disassembled form an implement portion 270 that includes the spur gear articulation mechanism 240. A frame 272 is longitudinally attachable to the handle portion 20 (depicted in FIGS. 1 and 2) with a bushing 274 on its proximal end for rotatingly engagement thereto. A frame trough 276 formed by an opening 278 longitudinally aligned with the center of the frame 272 is longer than a firing connector 280 that slides longitudinally within the frame trough 276. The proximal end of the firing connector 280 rotatingly engages the distal end of the metal drive bar 140 (depicted in FIG. 6). The distal end of the firing connector 280 includes a slot 282 that receives a proximal end of the firing bar 14, attached therein by pins 284. A more distal portion of the firing bar 14 is positioned within a lower groove 286 in a firing bar slotted guide 288 that is distally engaged with an articulating frame member 290 and the frame 272.

Articulating frame member 290 has a channel-anchoring member 292 that distally attaches to an attachment collar 294 of a proximal portion in the elongate channel 16. The firing bar 14 passes through a lower slot 295 in the articulating frame member 290. The articulating frame member 290 is spaced away from the distal end of the frame 272 by the firing bar slotted guide 288 and flexibly attached thereto for articulation by a resilient connector 296. A widened proximal end 298 of the resilient connector 296 engages a distally communicating top recess 300 in the distal end of the frame 272 and a widened distal end 302 of the resilient connector 296 engages a proximally communicating top recess 304 in the articulating frame member 290. Thereby, the elongate channel 16 is attached to the handle portion 20, albeit with a flexible portion therebetween.

The elongate channel 16 also has an anvil cam slot 306 that pivotally receives an anvil pivot 308 of the anvil 18. The closure ring 250 that encompasses the articulating frame member 290 includes a distally presented tab 310 that engages an anvil feature 312 proximate but distal to the anvil pivot 308 on the anvil 18 to thereby effect opening. When the closure ring 250 is moved forward, its distally presented closing face 314 contacts a ramped cylindrical closing face 316, which is distal to tab 312 of the anvil 18. This camming action closes the anvil 18 downward until the closing face 314 of the closure ring 250 contacts a flat cylindrical face 318 of the anvil 18.

Tapered Firing Bar

Figure 12:
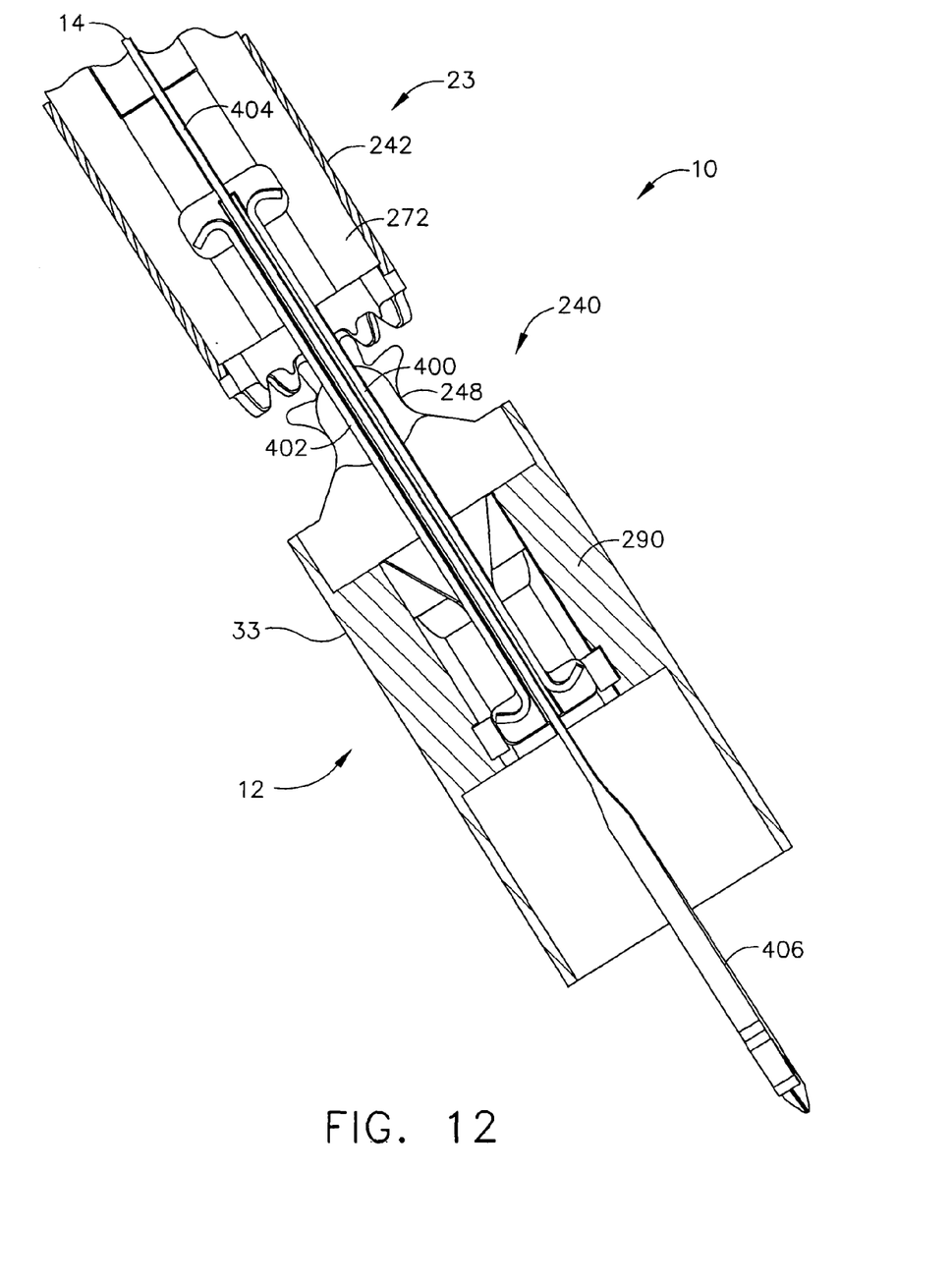
FIG. 12 depicts a top sectional view of the spur gear articulation mechanism of FIG. 11.

FIG. 12 depicts the articulation mechanism 240 along the articulation pivot axis illustrating flexible support structures between the shaft 23 and the end effector 12 and a construction of the firing bar 14 that advantageously performs severing yet is flexible enough for articulation. The hollow articulation drive tube 242 engages the spur gear 248 of the closure ring 33 (only the spur gear 248 of the closure ring 33 being depicted). Omitted from this view are the proximal portion, or closure tube 35, of the closure sleeve 32 that longitudinally position for articulation the spur gear 248.

Resilient support in the articulation mechanism 240 allow articulation about the articulation pivot axis includes a pair of support plates 400, 402 that provide lateral guides to a proximal portion of the firing bar, depicted as an elongate tapered firing bar strip 404 aligned for flexing about the articulation pivot axis. This tapered firing bar strip 404 transitioned to a thicker distal portion, depicted as a firing bar head 406, that includes the cutting edge 48, upper pin 38, middle pin 46 and firing bar cap 44. The thinner portion of firing bar strip 404 is easier to bend than the thicker portion 406, thereby reducing the force to articulate the end effector. This thicker firing bar head 406 has increased thickness to resist deflection from tissue clamping loads during firing, thereby ensuring an effective severing and actuation of the staple cartridge 37.

Operation

A closed end effector 12 and shaft 23 of an implement portion 22 of a surgical stapling and severing instrument 10 are inserted through a cannula passageway of a trocar to a surgical site for an endoscopic or laparoscopic procedure. The articulation control 13 is rotated as desired about the longitudinal axis of the shaft 23 to effect a corresponding rotation of the end effector 12. Advantageously, the actuator lever 202 of the articulation control 13 is pivoted to create a rotation articulation motion in an articulation drive tube 200, 242 that is converted into an articulation motion at a geared connection in an articulation mechanism 11, 240 thereby positioning the end effector 12 in a desired position. The firing bar 14 is advanced through the implement portion 22 to actuate the end effector 12, advantageously assisted through the articulation mechanism 11, 240 by including the elongate tapered firing bar strip 404 that flexes with reduced resistance.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

The present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For another example, although the E-beam firing beam 14 has advantages for an endoscopically employed surgical severing and stapling instrument 10, a similar E-Beam may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For yet another example, although an illustrative handle portion 20 described herein is manually operated by a clinician, it is consistent with aspects of the invention for some or all of the functions of a handle portion to be powered (e.g., pneumatic, hydraulic, electromechanical, ultrasonic, etc.). Furthermore, controls of each of these functions may be manually presented on a handle portion or be remotely controlled (e.g., wireless remote, automated remote console, etc.).

As yet an additional example, although a simultaneous stapling and severing instrument is advantageously illustrated herein, it would be consistent with aspects of the invention rotationally controlled articulation with other types of end effectors, such as grasper, cutter, staplers, clip applier, access device, drug/gene therapy delivery device, and a energy device using ultrasound, RF, laser, etc.

For example, although a spur gear articulation mechanism 240 is illustrated herein, it that other articulation mechanisms may be included, such as those described in the aforementioned co-pending applications.

As an additional example, for articulation mechanisms that obstruct the longitudinal axis of the shaft, the support plates and tapered firing bar strip may be offset from the longitudinal axis.

What is claimed is:

1. A surgical instrument, comprising:
   a handle portion operably configured to produce a rotational articulation motion and a longitudinal firing motion;
   a shaft operably configured to separately transfer the rotational articulation motion and the longitudinal firing motion;
   an end effector distally coupled to the shaft;
   an articulation mechanism responsive to the rotational articulation motion to articulate the end effector; and
   a firing bar responsive to the longitudinal firing motion of the handle portion, the firing bar comprising:
      an elongate strip longitudinally positioned for movement through the articulation mechanism and laterally aligned with an axis of articulation, and
      a firing bar head distally aligned with, thicker than, and connected to the elongate strip and positioned for longitudinal movement in the end effector,
      wherein the elongate strip has a width aligned with an axis of articulation substantially larger than a thickness of the elongate strip transverse to the axis of articulation, thereby operably configured to resiliently bend about the axis of articulation while resisting pivoting in a lateral axis orthogonal to both the longitudinal and articulation axes.

2. The surgical instrument of claim 1, wherein the handle portion comprises a handle means for producing a rotational articulation motion and a longitudinal firing motion, and the shaft comprises a shaft means for separately transferring the rotational articulation motion and the longitudinal firing motion, and wherein the articulation mechanism responds to the rotational articulation motion by articulating the end effector in an articulation plane bisected by a longitudinal axis of the shaft.

3. The surgical instrument of claim 2, wherein the handle means further comprises a means for producing a longitudinal closing motion, and the shaft means further comprises a means for separately transferring the longitudinal closing motion.

4. A surgical instrument comprising:
   a handle portion operable to produce a firing motion, a closing motion, and an articulation motion;
   a shaft coupled to the handle portion operable to separately transfer the firing motion, the closing motion, and the articulation motion;
   an elongate channel coupled to the shaft and including a channel slot,
   an anvil pivotally coupled to the elongate channel, responsive to the closing motion from the shaft, and including an anvil channel;
   a firing device including a distally presented cutting edge longitudinally received between the elongate channel and the anvil; and
   an articulation mechanism pivoting the elongate channel from the shaft in response to the articulation motion;
   wherein the firing device includes a thinned strip portion transitioning through the articulation mechanism, wherein the firing motion is distally directed by the thinned strip portion to the cutting edge, and wherein the thinned strip portion has a width aligned with an axis of articulation substantially larger than a thickness of the thinned strip portion transverse to the axis of articulation, thereby operably configured to resiliently bend about the axis of articulation while resisting pivoting orthogonally to the longitudinal axis and articulation axis, the firing device having an increased thickness.

5. The surgical instrument of claim 4, wherein the shaft further comprises an articulation drive tube responsive to the rotational motion from the handle portion and distally terminating in a gear section, the articulation mechanism comprising a spur gear proximally attached to the end effector and engaged by the gear section.

6. The surgical instrument of claim 4, wherein the firing device is operatively configured to affirmatively space the anvil from the elongate channel during longitudinal travel between the anvil and elongate channel.

7. The surgical instrument of claim 6, wherein the firing device includes an upper feature slidingly engaged to the anvil and a lower feature slidingly engaged to the elongate channel to cause spacing therebetween during longitudinal travel.

8. The surgical instrument of claim 4, further comprising a staple cartridge engaged by the elongate channel and including a proximally opened slot for receiving the cutting edge of the firing device, the staple cartridge including a plurality of staples cammed upwardly by the distal longitudinal movement of the firing device.

9. The surgical instrument of claim 8, wherein the staple cartridge further includes a plurality of drivers supporting the plurality of staples and a wedge sled responsive to the distal longitudinal movement of the firing mechanism to cam upwardly the drivers and thus form the plurality of staples against the anvil.

10. The surgical instrument of claim 4, further comprising a closure member operatively configured to longitudinally transfer the closure motion to the end effector to inwardly bias distal ends of the anvil and the elongate channel to assist the firing device in affirmatively spacing the anvil and elongate channel during actuation of the staple cartridge.

* * * * *